United States Patent
Hsu

(10) Patent No.: US 9,326,689 B2
(45) Date of Patent: May 3, 2016

(54) THERMALLY TAGGED MOTION TRACKING FOR MEDICAL TREATMENT

(75) Inventor: Stephen J. Hsu, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 875 days.

(21) Appl. No.: 13/466,927

(22) Filed: May 8, 2012

(65) Prior Publication Data

US 2013/0303880 A1    Nov. 14, 2013

(51) Int. Cl.

| A61B 5/05 | (2006.01) |
|---|---|
| A61B 5/01 | (2006.01) |
| A61N 7/02 | (2006.01) |
| A61B 5/055 | (2006.01) |
| A61B 5/11 | (2006.01) |
| A61B 8/08 | (2006.01) |
| A61B 17/00 | (2006.01) |
| A61B 18/00 | (2006.01) |

(52) U.S. Cl.
CPC ............ *A61B 5/015* (2013.01); *A61B 5/055* (2013.01); *A61B 5/1114* (2013.01); *A61B 8/08* (2013.01); *A61B 8/5223* (2013.01); *A61N 7/02* (2013.01); *A61B 8/085* (2013.01); *A61B 8/5276* (2013.01); *A61B 2017/00106* (2013.01); *A61B 2017/00694* (2013.01); *A61B 2018/00791* (2013.01)

(58) Field of Classification Search
USPC ................. 600/407, 410–411, 427, 438–439
See application file for complete search history.

(56) References Cited

U.S. PATENT DOCUMENTS

| 5,682,331 | A | 10/1997 | Berlin |
| 2002/0118170 | A1 | 8/2002 | Iaria et al. |
| 2006/0293598 | A1 | 12/2006 | Fraser |
| 2007/0106157 | A1* | 5/2007 | Kaczkowski et al. ......... 600/438 |
| 2009/0017910 | A1 | 1/2009 | Rofougaran et al. |
| 2011/0060221 | A1 | 3/2011 | Fan et al. |

OTHER PUBLICATIONS

Arthur et al. Non-invasive estimation of hyperthermia temperature with ultrasound, 2005.*

* cited by examiner

*Primary Examiner* — Joel F Brutus

(57) ABSTRACT

Motion tracking is performed with a thermal pattern within a patient. A pattern of different temperature is created in tissue, such as warming up tissue in a checkerboard pattern. The temperature pattern is used over time to track motion of the tissue. The tracked motion may be used to treat the tissue throughout at least part of a periodic cycle.

20 Claims, 2 Drawing Sheets

THERMALLY TAGGED MOTION TRACKING FOR MEDICAL TREATMENT

BACKGROUND

The present embodiments relate to motion tracking. Tissue moves due to cardiac and/or respiratory forces. In guided medical procedures, tissue motion may negatively affect the procedure. For example, motion may cause application of radiation or therapy to miss, in part, the target.

The adverse effects of the motion may be avoided. For example, in abdominal high intensity focused (HIFU) therapy, the treatment is gated with respiration. A breathing sensor detects the breathing cycle so that treatment is only provided a certain phase of the cycle. In another approach, the patient is asked to hold their breath during treatment to avoid motion. In yet another approach, motion tracking of the tissue may compensate and adjust the procedure to account for the motion, allowing more continuous dosing. If the internal motion is predicted or measured, the therapy dosing may follow the region of interest during the cycle for continuous dosing and corresponding shorter treatment times. For motion tracking, the motion of the tissue itself is tracked. In ultrasound, correlation-based motion estimation is performed. However, tissue-based motion estimation may be prone to error, especially in the presence of non-translational motion, such as rotation, scaling, or deformation.

BRIEF SUMMARY

By way of introduction, the preferred embodiments described below include methods, computer readable media, instructions, and systems for motion tracking in medical treatment. A pattern of elevated temperature is created in tissue, such as warming up tissue in a checkerboard pattern. The temperature pattern is used over time to track motion of the tissue. The tracked motion may be used to treat the tissue throughout at least part of a periodic cycle.

In a first aspect, a method is provided for motion tracking in medical treatment. Ultrasound is transmitted to a plurality of locations in a pattern in tissue within a patient. The tissue is heated in the pattern in response to the transmitting. An imaging system scans the tissue of the patient after the heating. A first spatial distribution of temperature in the tissue at a first time is detected. The first spatial distribution includes the pattern. A second spatial distribution of the temperature in the tissue at a second time is detected. The second spatial distribution includes the pattern. A change in position between the first and second times is determined from the first and second spatial distributions of the pattern.

In a second aspect, a non-transitory computer readable storage medium has stored therein data representing instructions executable by a programmed processor for motion tracking in medical treatment. The storage medium includes instructions for applying a thermal dose in a pattern to tissue within a patient, imaging temperature of the tissue over time, and determining position of the tissue as a function of the temperature of the tissue.

In a third aspect, a system is provided for motion tracking in medical treatment. A transmit beamformer connects with at least one transducer. The transmit beamformer is operable to transmit, with the transducer, high intensity focused ultrasound into a region. A receive beamformer connected with the at least one transducer. The receive beamformer is operable to receive data representing the region at different times. A detector is configured to determine temperature information in the region. A processor is configured to track a location in the region subjected to motion from a physiological cycle. The location is tracked with the temperature information.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the Figures, like reference numerals designate corresponding parts throughout the different views.

DETAILED DESCRIPTION OF THE DRAWINGS AND PRESENTLY PREFERRED EMBODIMENTS

Thermally-tagged motion tracking is provided. Tissue is thermally imprinted with a pattern. Using a thermal dosing device, a pattern is applied within the tissue. Then, a thermometry-based method is used to observe the temperature changes within the tissue. Changes in temperature are observable within ultrasound images via changes in speed of sound or other measure. As the tissue moves, the heating pattern should follow. By tracking the motion of the thermal pattern, the underlying tissue motion is determined.

Figure 1:
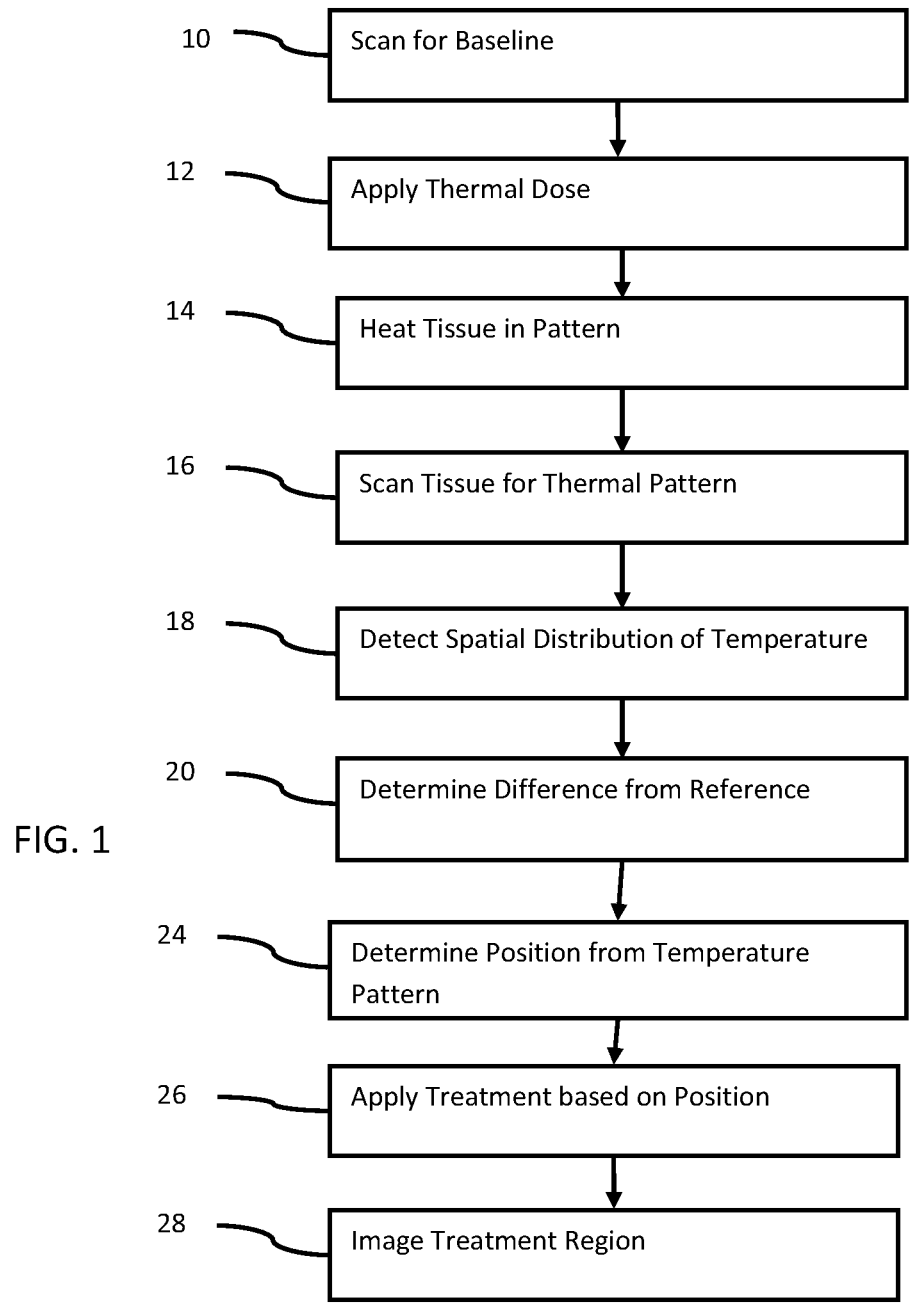
FIG. 1 is a flow chart diagram of one embodiment of a method for motion tracking using temperature in medical treatment.

FIG. 1 shows one embodiment of a method of motion tracking in medical treatment. The method tracks tissue during a periodic cycle using temperature information, such as absolute temperature or change in temperature. The method is implemented using the system of FIG. 3 or a different system.

Additional, different, or fewer acts may be provided. For example, acts 10 and/or 20 are optional. As another example, acts 26 and/or 28 are not performed. In another example, act 18 is for actively detecting the pattern or for merely having received data representing the pattern. The received data representing the pattern may be correlated to find motion without active detection of the pattern. The acts are performed in the order shown or a different order.

The method is performed for various applications. The motion tracking may be used for calibration, registration, transformation, guiding treatment, or other uses. The method is implemented as a thermometry method. Ultrasound, magnetic resonance (MR), or other modality for measuring temperature may be used. The method may be implemented for dealing with any form of periodic motion, such as respiratory or cardiac motion. Non-periodic motion or motion from non-physiological sources (e.g., from manual manipulation) may be thermally tracked.

In one embodiment, the method is implemented in respiratory motion-compensated HIFU therapy. In a therapy session for a given patient, the patient is readied for the therapy. A sonographer or physician places one or more transducers on the patient. Before the high intensity focused ultrasound (HIFU) begins for ablation or other treatment, any reference scans are performed in act 10. The motion tracking is then performed prior to treatment, such as determining typical or expected motion. The treatment may be guided in subsequent cycles based on the expected motion. In other embodiments, the motion tracking is interleaved with the therapy. The tissue position is determined using temperature and the application of treatment is guided based on the current position.

In act 10, an imaging system scans the tissue of the patient prior to motion tracking. The same imaging system used for motion tracking performs the scan. The same type of scan is used. For example, a scan for thermometry is performed.

The scan is of a region of tissue within the patient. The region is a line, area, or volume. The region is within the patient, such as below a surface of the skin. The region may be of all or part of an organ, such as a liver or kidney. The tissue may not be visible from outside the patient.

The scanning is for a given time. To scan a region, any format may be used. The region is sampled, such as along a plurality of ultrasound scan lines. While it may take multiple scans, repetition, or a period to scan the entire region, the resulting frame of data representing the line, area, or volume may represent a given time. Repetition to acquire a different frame of data may represent a different time.

The scanning may be repeated through all or a part of a periodic cycle. For example, the scanning is repeated to acquire frames of data representing the region of tissue at different phases through a breathing and/or heart cycle. Frames of data may be obtained for multiple cycles. Data representing the same locations at the same phase of the cycle, but acquired at different times (i.e., different cycles) may be kept separate or combined, such as averaged. In one embodiment, a sequence of frames of data is acquired through at least one entire breathing cycle. Any temporal resolution may be used, such as acquiring twenty five or more frames representing the tissue at different times in one cycle.

Any imaging system may be used. In one embodiment, the imaging system is a medical diagnostic ultrasound imaging system. The imaging system includes a transducer for scanning the patient. In another embodiment, the imaging system is a magnetic resonance system. Magnets and electrical pulses are used to detect the response of atoms or molecules. Other imaging modalities may be used, such as any modality capable of detecting the temperature or temperature change of the tissue. For example, both ultrasound and magnetic resonance systems may detect temperature information in tissue.

For ultrasound imaging, waveforms at ultrasound frequencies are transmitted, and echoes are received. The acoustic echoes are converted into electrical signals and beamformed to represent sampled locations within a region of the patient. The beamformed data may be filtered or otherwise processed. The beamformed data may be detected, such as determining intensity. A sequence of echo radio frequency signals from a same location may be used for correlation or to estimate velocity, variance, and/or energy. Echoes at one or more harmonics of the transmitted waveforms may be processed. The detected values may be filtered and/or scan converted to a display format. The ultrasound data representing the patient is from any point along the ultrasound processing path, such as channel data prior to beamformation, radio frequency or in-phase and quadrature data prior to detection, detected data, or scan converted data.

For magnetic resonance, the received data indicates projection intensities. Using tomography or other processing, the intensity of response from different locations is determined. Different pulse sequences may be used to detect different molecules and/or characteristics at the scan region.

The scan provides one or more frames of reference data. The data may be image data, such as data that may be used or is used to generate an image. The reference is acquired before any thermal dose or after a thermal dose but before another thermal dose.

The reference frame or frames of data represent temperature information. The baseline temperature information for detecting a change is detected. By performing thermometry by scanning and detecting, the temperature of various locations may be determined. Thermometry images or data may be used as a reference before creating a thermal pattern in the tissue. Since the creation of the thermal pattern itself may create a motion artifact, reference information may be used to remove the artifact prior to motion detection. The reference provides a baseline.

Any temperature related measurement may be used. Ultrasound measurements may be provided for a plurality of different locations. Any now known or later developed temperature related measurement using ultrasound may be used. For example, tissue expands when heated. Measuring the expansion may indicate temperature. The reference indicates the current relative positions of tissue.

Temperature related measurements may directly or indirectly indicate a temperature. For example, a measure of a parameter related to conductivity or water content (e.g., a measurement of the type of tissue) may indirectly indicate the temperature. The measurements may be for raw ultrasound data or may be derived from ultrasound data. In one embodiment, two or more, such as all four, of tissue displacement, speed of sound, backscatter intensity, and a normalized correlation coefficient of received signals are performed. Other measurements are possible, such as expansion of vessel walls.

Tissue displacement is measured by determining an offset in one, two, or three-dimensions. A displacement associated with a minimum sum of absolute differences or highest correlation is determined. The current scan data is translated, rotated, and/or scaled relative to a reference dataset, such as a previous or initial scan. The offset associated with a greatest or sufficient similarity is determined as the displacement. B-mode or harmonic mode data is used, but other data may be used. The displacement calculated for one location may be used to refine the search or search region in another location. Other measures of displacement may be used. Temperature change may be estimated from the displacement. The reference frames of data provide the baseline for comparison of displacement.

The speed of sound may be measured by comparison in receive time from prior to heating with receive time during heating. A pulse is transmitted. The time for the echo to return from a given location may be used to determine the speed of sound from the transducer to the location and back. Any aperture may be used, such as separately measuring for the same locations with different apertures and averaging. In another embodiment, signals are correlated. For example, in-phase and quadrature signals after beamformation are correlated with reference signals. A phase offset between the reference and current signals is determined. The frequency of the transmitted waveform (i.e., ultrasound frequency) is used to convert the phase difference to a time or speed of sound. Other measurements of the speed of sound may be used. Temperature may be measured from the speed of sound. The reference frame of data may be used as a baseline for the speed.

The backscatter intensity is B-mode or M-mode. The intensity or energy of the envelope of the echo signal is determined.

Temperature may be measured from the intensity. The baseline frames of data may be used to determine a change in intensity due to temperature.

The normalized correlation coefficient of received signals may be measured. Beamformed data prior to detection, such as in-phase and quadrature data, is cross-correlated. In one embodiment, a reference sample or samples are acquired. During or after creation of the thermal pattern, subsequent samples are acquired. For each location, a spatial window, such as three wavelengths in depth, defines the data for correlation. The window defines a length, area or volume. The current data is correlated with the reference data within the window space. The normalized cross-correlation is performed for the data in the window. As new data is acquired, further cross-correlation is performed. Temperature may be measured from the phase shift. Thermal strain may be measured from a derivative of the phase shift.

Any temperature associated acoustic and physical parameters or changes in the parameters may be measured. Other measurements include tissue elasticity, strain, strain rate, motion (e.g., displacement or color flow measurement), or reflected power (e.g., backscatter cross-section).

In one embodiment, the temperature is estimated from a model rather than directly measured. One or more of the types of information discussed above may be used as inputs to the model. In addition to the ultrasound scanning, clinical or other information may be acquired for determining the temperature. For example, genetic information or other tissue related data may be mined from a patient record. Any feature contributing to determination of temperature related information may be used.

Expansion, shrinkage, water content, or other therapy parameters may indicate a current temperature. Regardless of the categorization of the measurement, the measurements are used as inputs to a model or to calculate values for input to the model. The data is provided for one or more locations, such as providing data for all locations in a two- or three-dimensional region.

The temperature related measurements are applied to the model. The measurements or data are input as raw data. Alternatively, the values (i.e., measurements and/or data) are processed and the processed values are input. For example, the values are filtered spatially and/or temporally. As another example, a different type of value may be calculated from the values, such as determining a variance, a derivative, normalized, or other function from the values. In another example, the change between the current values and reference or previous values is determined. A time-history of the values over a window of time may be used. The values are input as features of the model.

The output of the model may be used as an input. The values are applied during the application of the sample. For an initial application of the model, the feedback is replaced with a reference temperature, such as the temperature of the patient. For further application of the model, the previous output is fed back as an input, providing a time-dependent model. The temperature related information output by the model is fed back as a time history of the information, such as temperature at one or more other times. After creating the thermal pattern, the measured or received values are updated (i.e., current values are input for each application of the model), but previous values may also be used. The feedback provides an estimated spatial distribution of temperature or related information in the region at a previous time. The subsequent output of the model is a function of the ultrasound data or other values and a previous output of the modeling. The time-history of the values may be used as inputs, such that the time history and spatial distributions of the temperature-associated and therapeutic effect-related parameters are used as features of the model. In alternative embodiment, no feedback is used.

The model outputs a temperature or temperature distribution (i.e., temperature at different locations and/or times) from the input information. The derived temperature may be in any unit, such as degrees Fahrenheit or Celsius. The resolution of the temperature may be at any level, such as outputting temperature as in one of multiple two or other degree ranges. Alternatively, other temperature related information is output, such as a change in temperature, a dose, or an index value.

Any model may be used, such as a neural network or a piecewise linear model. The model is programmed or designed based on theory or experimentation. In one embodiment, the model is a machine-learned model. The model is trained from a set of training data labeled with a ground truth, such as training data associated with actual temperatures. For example, the various measures or receive data are acquired over time for each of multiple patients. During transmission of the sample therapy, the temperature is measured. The temperature is the ground truth. Through one or more various machine-learning processes, the model is trained to predict temperature given the values and/or any feedback.

Any machine-learning algorithm or approach to classification may be used. For example, a support vector machine (e.g., 2-norm SVM), linear regression, boosting network, probabilistic boosting tree, linear discriminant analysis, relevance vector machine, neural network, combinations thereof, or other now known or later developed machine learning is provided. The machine learning provides a matrix or other output. The matrix is derived from analysis of a database of training data with known results. The machine-learning algorithm determines the relationship of different inputs to the result. The learning may select only a sub-set of input features or may use all available input features. A programmer may influence or control which input features to use or other performance of the training. For example, the programmer may limit the available features to measurements available in real-time. The matrix associates input features with outcomes, providing a model for classifying. Machine training provides relationships using one or more input variables with outcome, allowing for verification or creation of interrelationships not easily performed manually.

The model represents a probability of temperature related information. This probability is a likelihood for the temperature related information. A range of probabilities associated with different temperatures is output. Alternatively, the temperature with the highest probability is output. In other embodiments, the temperature related information is output without probability information.

As an alternative to machine learning, manually programmed models may be used. The model may be validated using machine training. In one embodiment, a thermal distribution model is used. The thermal distribution model accounts for the thermal conductivity, density, or other behavior of different tissues, fluids, or structures. The thermal distribution model receives temperatures, temperature related information, measurements, or other data. The input information may be sparse, such as having temperature information for one or more, but fewer than all locations. The thermal distribution model determines the temperature at other locations. The thermal distribution model may determine the temperature at other times or both time and location.

In another embodiment, the thermal distribution model corrects temperatures based on anatomy. For example, a machine-learned model estimates temperature for uniform tissue. The temperature output is corrected to account for tissue differences in the region, such as reducing the temperature around thermally conductive vessels or fluid regions. In response to input of the features, the model outputs the temperature related information, such as temperature.

Non-real time measurements may be used, such as a baseline temperature. MRI-based measurements for temperature distribution in a region may be used. Real-time measurements may be used, such as associated with ultrasound measurements performed during application of thermal therapy to a region of the patient.

In act 12, a thermal dose is applied in a pattern to tissue within a patient. Any technique for heating tissue internal to a patient may be used. Radiation, x-rays, or ultrasound are used. For example, acoustic energy is transmitted. High intensity focused ultrasound therapy waveforms may be transmitted. For HIFU, the transmitted excitation is acoustic energy. The acoustic energy is focused, resulting in a three-dimensional beam profile with a focal location at a depth along the beam. The excitation is focused using a phased array and/or mechanical focus. The focus may be fixed or steerable. The excitation may be unfocused in one dimension, such as the elevation dimension. The excitation is transmitted into tissue of a patient. For a given transmission, a single beam is formed. Alternatively, multiple beams with respective foci are formed for a given transmission.

The excitation is generated as a therapy excitation. Alternatively, the excitation emulates the therapy excitation. A sample of the high intensity focused ultrasound therapy waveform is transmitted. A generally same focus, amplitude, frequency, and/or other characteristic as the therapy excitation are provided for the sample. The sample is used to substantially avoid therapeutic effect. For example, the amplitude, duration, or both are reduced as compared to a therapy waveform (e.g., Isppa on the order of about 200 W/cm$^2$ and duration on the order of about 600 micro seconds). "Substantially" avoiding therapeutic effect allows for generalization to a region, such as the region of treatment. A single point may be heated above a threshold level due to aberrations or focal distortion, but the treatment region overall avoids therapeutic effect from the emulation. Avoiding therapeutic effect may be avoiding heating to the point of altering the tissue or creating cavitations. For example, biological effects may include hyperthermia at tissue temperature of about 41-45° C., protein denaturation at temperatures above 45° C., and tissue necrosis at temperatures above 50° C. Tissue stiffness may be affected even at temperatures below 45° C. At temperatures above 45° C., increases in viscosity and/or stiffness may occur. At temperatures above 50° C., the tissue may have a high stiffness and/or high attenuation. Any limit on the emulation may be provided, such as attempting to prevent a temperature increase of five degrees or more Celsius.

The high intensity focused ultrasound therapy waveform causes a detectable response in the tissue. For example, the temperature at the focal region increases by 1-4 degrees, such as increasing about 2-3 degrees. At other locations than the focus, the temperature may increase less or not at all in response to the HIFU. In alternative embodiments, a lower dose of the therapy waveform causes some therapeutic effect, such as increasing stiffness (e.g., raise the temperature to about 45° C.), but avoids other therapeutic effect (e.g., avoids raising the temperature to 50° C. or higher). The elasticity, strain, or stiffness of the tissue changes.

By repeating transmission to different locations, a thermal pattern is created in the patient. Any sequence may be used to create any pattern. For example, transmissions are repeated while altering the focus along one or more lines. A plurality of beams is generated to form the pattern. A thermal dose is applied to produce a specific thermal pattern within tissue.

Figure 2:
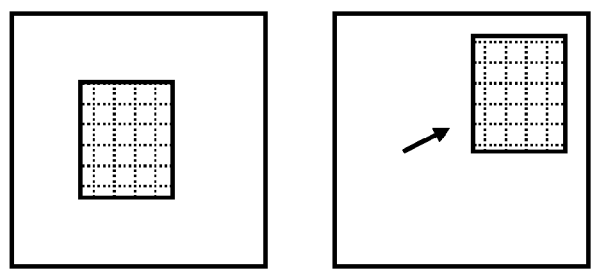
FIG. 2 illustrates tracking of a temperature pattern according to one embodiment.

Any pattern may be used. For example, a pattern of one or more points of increased temperature is created. As another example, one or more intersecting or parallel lines of increased temperature are created. A checkerboard pattern may be created. Curves may be used. Lines or other continuous segments may be emulated by heating points along the segment. FIG. 2 shows a crossing pattern of line where the lines are formed by heating points. In another embodiment, the region to be treated is used as the pattern.

In act 14, the tissue heats. The locations associated with the application of the energy are heated. Due to thermal dispersion, the heating may spread. In the time frame of one or a few heart or breathing cycles, the temperature increase may spread. The locations associated with the pattern may maintain an elevated temperature for seconds or tens of seconds, depending on proximity of blood or other thermal conductors. Other locations may be heated less or not at all during that time frame.

The pattern of heating may be created in a fraction of a second. The heating may occur in a short enough period that motion of the tissue is minimal during the heating. Alternatively, the patient holds their breath and/or cycle gating is used for heating the tissue.

In acts 16 and 18, temperature information is imaged. The temperature information may be imaged without generating an image. For example, the tissue is scanned in act 16 and spatial distribution of temperature detected in act 18 without generating an image. An image of temperature may alternatively be generated.

The imaging is thermometry. Ultrasound, MR, or other thermometry may be used. For example, one of the techniques using ultrasound measures discussed above is used to determine a temperature change or an absolute temperature. Any imaging method capable of measuring thermal changes or absolute temperature within tissue may be used to track motion.

A frame of data representing temperature information is acquired. For motion tracking, frames are acquired from different times. The frames may represent the temperature information at different times or phases during a same cycle. For example, a sequence of frames of temperature data is acquired during one or more breathing cycles. The thermometry is performed at different times during the physiological cycle. Where reference information is acquired for a cycle prior to the heating, these subsequent frames after the heating are frames for one or more subsequent sequences of the breathing cycle.

In act 16, an imaging system scans the tissue of the patient after the heating. For example, an ultrasound or magnetic resonance system scans in a thermometry mode. Any of the scanning discussed above for act 10 may be used. Since this scanning occurs after the heating, the received data represents the pattern as well as the temperature of tissue not used to create the pattern. The received data represents tissue with elevated temperatures at some locations and not others.

In act 18, a spatial distribution of temperature in the tissue is detected. The spatial distribution includes the pattern. Detection of the spatial distribution is detection of the temperatures for the frame of data without specifically identifying which locations are part of the pattern. The scanning provides received signals. By detecting the temperature from the measurements, the spatial distribution is detected. The temperature is detected as an absolute value (e.g., 101° F.), as a change from a previous temperature at the same location (e.g., 3° F.), or as higher than surrounding locations (e.g., spatial change).

In one embodiment, the thermal strain is detected as the temperature information. For example, radio frequency data (e.g., in-phase and quadrature data) after beamformation and before any detection is acquired for each location at different times. The phase shift over time (e.g., a current signal compared to a reference or baseline signal acquired in act 10) represents a time lag due to change in speed of sound. The phase shift is determined by correlating the data from different times. A one, two, or three-dimensional window is applied to each set of data for correlation. The correlation is used to find the phase shift. The speed of sound changes with temperature. The first derivative of the phase shift provides the thermal strain.

In other embodiments, the spatial distribution is detected as the pattern. The locations with elevated temperature are identified or distinguished from other locations. The locations of elevated temperature are distinguished from other locations. For example, gradient filtering is applied to the detected temperature information. Directional filtering or pattern matching may be used to locate the pattern in the tissue.

Locations where the temperature or temperature change is relatively high are identified by applying a threshold. The threshold may be preprogrammed or adapted to a given data set. The threshold may be normalized, such as a threshold based on data at spatial locations spaced away from the likely location of the elevated temperature. As another example, an average or other percentage displacement or temperature across a region of interest is determined. Locations associated with a maximum displacement or temperature greater than the average or other percentage indicates locations of elevated temperature.

The temperature data may or may not be spatially filtered prior to application of the threshold. The displacements or temperatures may be low pass filtered after application of the threshold. In other or additional embodiments, no threshold is applied, or a noise threshold is used.

The identified locations are used to determine the location of the pattern. The distribution indicates the shape of the pattern as affected by any aberrations, tissue differences, thermal diffusion, or other deviations from ideal. Any manual, semi-automatic, or automatic approach to detecting the pattern may be used.

The pattern is determined within an area or a volume. For example, the pattern is determined using temperatures representing a volume. The location of the pattern may be determined in a one dimensional region, such as the location being along a line. Temperature is measured for just the line or area, but may be measured for regions with additional dimensions even if not used to detect the pattern.

The detection of the spatial distribution is performed for multiple frames of received signals. The detection of the pattern itself and/or the detection of temperatures representing different locations occurs using frames of data from different times. From a sequence of images or other frames of received data, the spatial distribution of the heating over time is determined. As the tissue moves, the heated portions of the tissue also move.

In act 20, a difference between the baseline acquired in act 10 or another time (e.g., after heating) and the data acquired in act 16 is determined. The heating may create an artifact motion. Where the temperature information is detected using a difference from a previous baseline, other differences than from the heating may result. By also subtracting out the baseline of the resulting temperature information, this artifact may be removed.

The temperature information from the baseline is subtracted from the detected temperature information acquired after heating. Data representing a same phase of the cycle is used for the difference.

Any difference operation may be used. For example, the temperature information is low pass filtered. The resulting temperature information from the baseline is then subtracted from the temperature information acquired after heating. As another example, a ratio or other function is used to indicate the difference.

In an alternative embodiment, the difference between the baseline and the current data provides the spatial distribution of the temperature. This difference is performed for act 18 without processing of act 20.

After any processing, the position of tissue is determined. The position is determined over time in act 24 by tracking the pattern. The spatial distribution of the temperature of the tissue is used to track motion over time. Frames of temperature information from different times are compared to determine the motion between the two frames. The spatial distribution of temperature for each frame is matched to a reference frame or other frame. The reference frame for motion tracking may be a frame from after heating at a particular phase of the cycle. Thermometry images representing the pattern are compared to track tissue motion.

When act 20 has been performed, the frames of temperature information are the results of having subtracted out the baseline temperature information. Other processing to highlight the pattern may be used, such as calculating gradients or high pass filtering.

The motion of the heating pattern is taken to reflect the motion of the underlying tissue. The thermal data is used to determine the motion of the specific heating pattern. Motion is tracked using correlation estimators. Similarities between frames of data from different times are calculated. For any two frames of data, different translations, rotations, scales, or combinations thereof are applied and a similarity is calculated. A correlation, minimum sum of absolute differences, or other similarity measure is performed. The temperature information in frames from different times are relatively translated, rotated, and/or scaled. The translation, rotation, and/or scale resulting in the greatest correlation or minimum sum of differences are the motion vector.

FIG. 2 shows the temperature information in a grid pattern in two frames. The pattern is shifted upward and to the right from the first to the second frame. By shifting, rotating, and/or scaling the frames relative to each other, the vector showing the motion between the two frames is calculated. In the example of FIG. 2, the pattern translates without any rotation, scaling, or deformation.

The motion tracking is performed with the spatial distribution of temperature information. Without detecting the pattern itself, the detected spatial distribution is used to track motion by correlation. In other embodiments, the pattern itself is used for tracking. The detected pattern may be replaced with a model, fitted, or idealized pattern. The detected pattern may be used for warping or determining non-linear distortion or motion.

Rigid (e.g., affine) or non-rigid motion tracking may be used. A deformation may be provided in addition to translation, rotation, and/or scaling. The deformation may be due to some tissue moving differently from other tissue. The calculated motion is a matrix, spline or other non-linear representation of the relationship between patterns from different times.

The motion of the spatial distribution of the temperature information is used as the motion of the tissue. The same tissue used for the pattern or adjacent tissue is treated as having moved the same as the thermal pattern. Tracking the motion of the thermal pattern through a sequence of frames or over time provides for tracking of the location of a treatment region of the tissue over time. The position of the thermal pattern is used to track the location of the treatment.

In act 26, treatment is applied to the tracked tissue. The change in position is used to change the location to which the treatment is applied. By accounting for motion through a cycle, the same tissue may be treated through the cycle despite having shifted relative to the source of treatment. By tracking the thermal pattern, a HIFU dosing pattern may then be programmed to compensate for the tissue motion and be synchronized with respiration in real-time or on a following breath.

The motion tracking and treatment guiding occur together. As the motion of the tissue is determined for a given phase, the treatment is guided for that phase to the correct tissue. Where the treatment uses heating of the tissue, the motion tracking may account for heating due to the treatment. For example, the treatment dose is treated as part of the pattern. The treatment dosing pattern may be used as the pattern to be tracked. Alternatively, the heating from the treatment is removed from the spatial distribution and/or the thermal pattern for tracking is spaced from the location for treatment.

Predictive motion may be used as well. A trend in the current motion (e.g., most recent motion) or a trend from previous cycles at the current phase may be used to predict the location of the tissue given the amount of time to aim and apply the treatment after scanning to determine motion. In other embodiments, predictive motion from tracking in a previous cycle or cycles is used to guide the treatment without motion tracking in the cycle in which treatment is applied.

For HIFU therapy, a therapy waveform is transmitted. The location of the focus, origin, scan line, or application of the therapy is based on the motion determined from tracking the thermal pattern. The coordinates in the therapy system for the treatment location of the patient may be registered to the ultrasound system used for tracking. Alternatively, the same system is used for tracking and therapy so that calibration or registration of coordinates may be avoided. The dose, angle, focus, and/or other characteristics of the therapy are established for the treatment location.

In the HIFU embodiment, high intensity focused ultrasound therapy waveforms are transmitted. High voltage waveforms are applied to the high intensity focused ultrasound transducer, which generates the HIFU therapy waveforms in the acoustic domain. The HIFU pulse or pulses are focused using a phased array and/or mechanical focus and provide the high intensity acoustic energy to tissue at a focal or beam location.

The therapeutic ultrasound pulse has a plurality of cycles at any desired frequency and amplitude. In one embodiment, the therapeutic pulse lasts for a fraction of a second to seconds at an ultrasound frequency, such as 500 KHz-20 MHz. Any peak intensity may be provided, such as 100 or more watts per square centimeter, 500 or more watts per square centimeter, 1000-2000 watts per square centimeter, or about 1000 watts per square centimeter. Any now known or later developed therapeutic waveform with any intensity, frequency, and/or number of cycles may be used. The waveform is continuous or intermittent.

The therapeutic ultrasound pulse treats the tissue by generating heat at the desired tissue location. The intensity also generates stress on the tissue. The pulse pushes the tissue towards and away from the transducer with negative and positive acoustic pressures. For a sufficiently long therapeutic pulse, a substantially constant strain on the tissue is created. The strain, $\epsilon$, is a function of the tissue stiffness, E, the viscosity, $\eta$, and the stress from HIFU radiation force. The steady state stress during the therapeutic pulse is proportional to the ratio of average HIFU intensity, I, to the speed of sound in the tissue, c.

The HIFU waveforms may also generate biomechanical changes. The thermal effects of the therapy acoustic energy may cause changes in volume due to thermal expansion, in the speed of sound (c), in tissue stiffness (E), and/or in the viscosity ($\eta$) of fluids in the tissue. The therapy acoustic energy may also induce mechanical effects, such as radiation pressure, streaming, and/or cavitations. The biological effects may include hyperthermia at tissue temperature of about 41-45° C., protein denaturation at temperatures above 45° C., and tissue necrosis at temperatures above 50° C. Tissue stiffness may be affected even at temperatures below 45° C. At temperatures above 45° C., increases in viscosity and/or stiffness may occur. At temperatures above 50° C., the tissue may have a high stiffness and/or high attenuation.

By using non-rigid motion tracking, the deformations caused by increasing stiffness in tissue are accounted for in the motion tracking. Alternatively, the motion is tracked without accounting for the effect of the treatment.

The HIFU may be continuous or sporadic. Any treatment regimen may be used. During ongoing treatment or in between different fractions of the treatment, the tracking is performed. The therapy waveforms of act 26 are interleaved with the scanning act 16. The HIFU treatment ceases while the scanning to detect the spatial distribution of temperature information is performed. In another alternative, the HIFU is performed at one frequency or coding, and the transmission and corresponding reception for scanning are performed at a different frequency or coding, allowing operation at the same time. The interleaving allows user or system positioning of the HIFU beam on an on-going basis. As the tissue shifts, the treatment shifts. If the patient or transducer shifts position, the beam may be altered to treat the appropriate tissue.

The motion tracking may be used for other actions than application of therapy. For example, motion tracking using the thermal pattern may be used to form an extended field of view or volume acquisition. The transducer moves instead of the tissue. The motion of the transducer is determined from the relative offsets at different times of the stationary thermal pattern. The thermal pattern appears to move due to the transducer motion. The differences in position for different scans may be used to assemble the frames of data into the extended field of view or volume.

In act 28, an image is displayed. The image is acquired by the imaging system. The image is of a two-dimensional region of the patient. Alternatively, the image is a three-dimensional representation (i.e., two-dimensional image rendered from data representing a volume). In other embodiments, the image represents one spatial dimension (e.g., M-mode) or represents a sampling of individual range gates over time (e.g., spectral Doppler at one or more locations).

Any type of image may be used, such as a B-mode, color flow mode (e.g., Doppler velocity, energy, and/or variance), tissue Doppler, M-mode, spectral Doppler, harmonic mode, contrast agent, perfusion, elasticity, strain, strain rate, shear velocity, modulus, parametric, or other now known or later developed imaging. In one embodiment, anatomical information is displayed, such as a B-mode or harmonic B-mode image. Where the imaging system is a magnetic resonance system, other types of images may be provided.

The image may include the temperature related information. The temperature information of the pattern may be displayed. Temperature information measuring the effects of treatment may alternatively or additionally be displayed.

The temperature related information is displayed as a value, such as a temperature or dose. A graph of temperature as a function of time or along a line may be displayed. In one embodiment, the temperature is mapped to color and overlaid on a two-dimensional image or a three-dimensional representation. The mapping modulates the color as a function of the temperature related information, such as the shade of red or color between red and yellow being different for different temperatures. The change in temperature may alternatively be mapped to the output color or additionally mapped to brightness or other aspect of the color. The overlay is laid over an ultrasound image representing the anatomy, such as overlaid on a B-mode image. The overlay is registered to the anatomic information. The overlay indicates a current location of the pattern or the focus for the therapy system, and the underlying anatomical image may show the anatomy to be treated.

Figure 3:
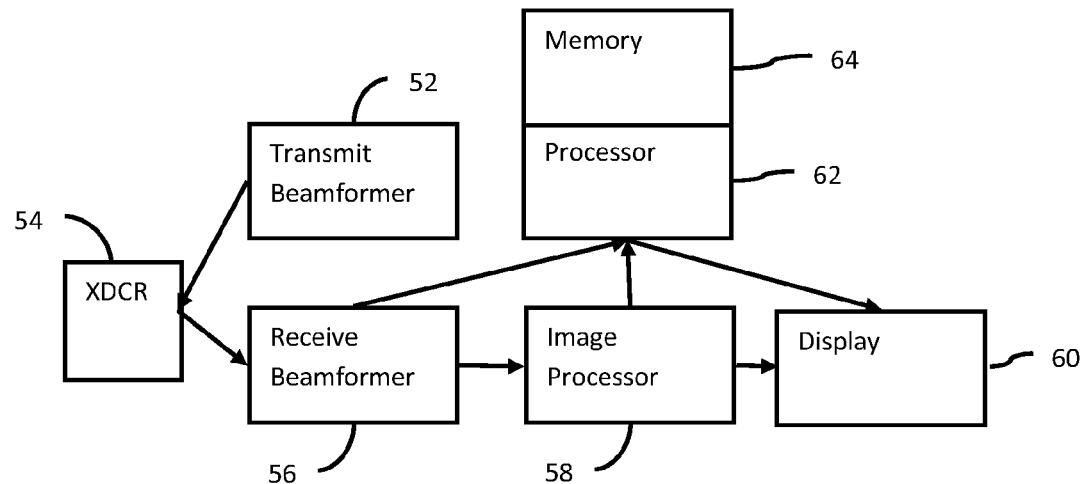
FIG. 3 is a block diagram of one embodiment of a medical diagnostic ultrasound imaging system for motion tracking by temperature.

FIG. 3 shows an ultrasound system for motion tracking in medical treatment. The system includes a transmit beamformer 52, a transducer 54, a receive beamformer 56, an image processor 58, a display 60, a processor 62 and a memory 64. Additional, different or fewer components may be provided. For example, separate detectors and a scan converter are also provided. As another example, a separate transmit beamformer is provided for therapy.

The ultrasound system is a medical diagnostic ultrasound imaging and/or therapy system. Imaging includes two-dimensional, three-dimensional, B-mode, Doppler, color flow, spectral Doppler, M-mode or other imaging modalities now known or later developed. The ultrasound system is a full size cart mounted system, a smaller portable system, a hand-held system or other now known or later developed ultrasound imaging system. In another embodiment, the processor 62 and memory 64 are part of a separate system. For example, the processor 62 and the memory 64 are a workstation or personal computer operating independently of the ultrasound system. As another example, the processor 62 and the memory 64 are part of a separate therapy system.

The system of FIG. 3 combines the imaging and therapy into one system. In other embodiments, the systems are separate or of a different modality even if combined. For example, the imaging system is a magnetic resonance, diagnostic ultrasound, x-ray, computed tomography or other imaging system. The therapy system is a HIFU system, microwave system, radiation system, or other source of transmitted therapeutic energy. Some components may be shared, such as processing electronics. In one embodiment, separate transducers are used, but otherwise the processing is performed by a common system.

The transducer 54 includes one or more transducers. The transducer is any now known or later developed transducer for generating high intensity focused ultrasound from electrical energy and/or for ultrasonically scanning for temperature information. A single element may be provided, such as where focus is provided mechanically by movement or a lens. A plurality of elements in a one or multi-dimensional array may be used, such as an array of N×M elements where both N and M are greater than 1 for electric based focusing or steering. The element or elements are piezoelectric, microelectromechanical, or other transducer for converting between electrical and acoustic energies. Multiple different arrays may be used, such as one for therapy and another for scanning. The same transducer array may be used for both therapy and scanning.

The transducer 54 is operable from outside a patient. For example, the transducer 54 is a probe or other device held against the patient's skin. The transducer 54 is handheld, positioned by a device, or strapped to the patient. In other embodiments, the transducer 54 is in a probe, catheter or other device for operation from within a patient.

In one embodiment, only one transducer 54 is provided. In other embodiments, a plurality of transducers 54 is provided. For example, a plurality of two-dimensional arrays of elements is used for transmitting from different locations to a treatment region.

Each of the transducer elements connect to the transmit beamformer 52 for receiving electrical energy from the transmit beamformer 52. The transducer 54 converts the electrical energy into an acoustic beam for therapy and forming a thermal pattern. For scanning, the transducer 54 converts received echoes into electrical signals.

The transmit beamformer 52 is one or more ultrasound transmitter, memory, pulser, waveform generators, amplifiers, delays, phase rotators, multipliers, summers, digital-to-analog converters, filters, combinations thereof and other now known or later developed transmit beamformer components. The transmit beamformer 52 is configured into a plurality of channels for generating transmit signals for each element of a transmit aperture. The transmit signals for each element are delayed and apodized relative to each other for focusing acoustic energy along one or more scan lines. Signals of different amplitudes, frequencies, bandwidths, delays, phases, durations, number of cycles, spectral energy distributions, or other characteristics are generated for one or more elements during a transmit event.

The transmit beamformer 52 connects with the transducer 54. In one embodiment, the same transmit beamformer 52 is used for therapy, creating the thermal pattern in tissue, and scanning. In other embodiments, different or separate transmit beamformers 52 and/or transducers 54 are used.

For scanning, the transmit beamformer 52 transmits a plurality of beams in a scan pattern. Upon transmission of acoustic waves from the transducer 54 in response to the generated waves, one or more beams are formed. A sequence of transmit beams are generated to scan a two or three-dimensional region. Sector, Vector®, linear, or other scan formats may be used. The same region is scanned multiple times. For flow or Doppler imaging and for strain imaging, a sequence of scans is used. In Doppler imaging, the sequence may include multiple beams along a same scan line before scanning an adjacent scan line. For strain imaging, scan or frame interleaving may be used (i.e., scan the entire region before scanning again). For thermometry, the sequence may be different depending on the type of measurement. In alternative embodiments, the transmit beamformer 52 generates a plane wave or diverging wave for more rapid scanning.

For therapy, the transmit beamformer 52 transmits one or more beams. To generate the pattern for tracking, the acoustic beams are high intensity focused ultrasound waveforms transmitted to different locations. A lesser aperture, amplitude, frequency or combinations thereof than used for therapy may be used to form the pattern.

For actual therapy, the transmit beamformer 52 causes generation of acoustic energy for HIFU. The high intensity focused ultrasound transducer 54 generates high intensity focused ultrasound therapy waveforms. Relative delays focus the acoustic energy. A given transmit event corresponds to transmission of acoustic energy by different elements at a substantially same time given the delays. The transmit event provides a pulse of ultrasound energy for treating the tissue. The transmit event may be repeated or may include on-going (multiple cycle) waveforms.

The receive beamformer 56 is configured to acquire ultrasound data representing a region of a patient. The ultrasound data is for measuring temperature related information, acquiring anatomical information, and/or receiving other data. The anatomical information is, at least in part, from ultrasound data.

The receive beamformer 56 includes a plurality of channels for separately processing signals received from different elements of the transducer 54. Each channel may include delays, phase rotators, amplifiers, filters, multipliers, summers, analog-to-digital converters, control processors, combinations thereof and other now known or later developed receive beamformer components. The receive beamformer 56 also includes one or more summers for combining signals from different channels into a beamformed signal. A subsequent filter may also be provided. Other now known or later developed receive beamformers may be used. Electrical signals representing the acoustic echoes from a transmit event are passed to the channels of the receive beamformer 56. The receiver beamformer 56 outputs in-phase and quadrature, radio frequency or other data representing one or more locations in a scanned region. The channel data or receive beamformed data prior to detection may be used by the processor 62.

The receive beamformer 56 receives signals for locations sampled in the scan pattern. By sampling a region, a frame of receive signals representing the region is acquired. By repeating the scanning, the receive beamformer 56 acquires frames of data representing the region at different times.

The receive beamformed signals are subsequently detected and used to generate an ultrasound image by the image processor 58. The image processor 58 is a B-mode/M-mode detector, Doppler/flow/tissue motion estimator, harmonic detector, contrast agent detector, spectral Doppler estimator, combinations thereof, or other now known or later developed device for generating an image or detecting data from received signals. The image processor 58 may include a scan converter. The detected or estimated signals, prior to or after scan conversion, may be used by the processor 62.

In one embodiment, the image processor 58 is a detector of temperature information. The receive signals may be processed to determine temperature information. For example, correlation and a derivative are performed to determine thermal strain from beamformed data. An absolute, change, or other temperature information is detected.

The processor 62 is a control processor, beamformer processor, general processor, application specific integrated circuit, field programmable gate array, digital components, analog components, hardware circuit, combinations thereof and other now known or later developed devices for processing information. The processor 62 is configured, with computer code, to track tissue motion using a thermal pattern. For example, the processor 62 controls scanning to acquire any baseline information, transmitting to form the thermal pattern in the tissue, scanning to measure temperature information, detecting to determine spatial distribution of the pattern, tracking to determine the motion of the tissue, and/or guiding therapy to the tracked location.

The processor 62 or the image processor 58 is configured to measure the temperature information. The temperature for different locations in the treatment region is estimated or calculated. In one embodiment, the temperature is estimated based on inputs to a model. The computer code implements a machine-learned model and/or a thermal model to estimate the temperature or temperature related information. The model is a matrix, algorithm, or combinations thereof to estimate based on one or more input features. In one embodiment, the processor 62 estimates temperature information as disclosed in U.S. Patent Application No. 2011/0060221, the disclosure of which is incorporated herein by reference. In other embodiments, the processor 62 uses measurements of one or more parameters to estimate temperature without a model.

The processor 62 is configured to track a location. The location is for treatment or for guiding treatment. The location is in the region subjected to motion from a physiological cycle. By tracking the thermal pattern created in the tissue, the translation, rotation, scaling, and/or warping caused by the tissue motion is identified. The treatment is guided to the desired tissue while accounting for the tissue motion. The location for treatment is tracked over time with the temperature information.

The memory 64 is a non-transitory computer readable storage medium having stored therein data representing instructions executable by the programmed processor for motion tracking in medical treatment. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 60 is a monitor, LCD, plasma, projector, printer, or other now known or later developed display device. The display 60 is configured to display an image representing the region of the patient, the thermal pattern, and/or the effect of thermal therapy. For example, an anatomy image is displayed. As another example, temperature or related information is output as a value, graph, or two-dimensional representation. The processor 62 and/or the image processor 58 generate display signals for the display 60. The display signals, such as RGB values, may be used by the processor 62.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method of motion tracking in medical treatment, the method comprising:

transmitting ultrasound to a plurality of locations in a pattern in tissue within a patient;
heating the tissue in the pattern in response to the transmitting;
scanning, with an imaging system, the tissue of the patient after the heating;
detecting first spatial distribution of temperature in the tissue at a first time, the first spatial distribution including the pattern;
detecting second spatial distribution of the temperature in the tissue at a second time, the second spatial distribution including the pattern; and
determining a change in position between the first time and the second time from the first spatial distribution and the second spatial distribution of the temperature caused by the pattern.

2. The method of claim 1 further comprising:
applying treatment to the tissue as a function of the change in position.

3. The method of claim 1 wherein transmitting comprises generating a plurality of beams to form the pattern as intersecting lines below a surface of a skin of the patient.

4. The method of claim 1 wherein heating comprises increasing the temperature at locations on the pattern by at least 2 degrees.

5. The method of claim 1 wherein scanning comprises scanning with an ultrasound or magnetic resonance system as the imaging system, the scanning comprising thermometry imaging.

6. The method of claim 1 wherein detecting the first spatial distribution and the second spatial distribution comprises calculating thermal strain.

7. The method of claim 1 wherein detecting the first spatial distribution and the second spatial distribution comprises identifying locations with elevated temperature.

8. The method of claim 1 wherein determining the change in the position comprises determining translation and rotation.

9. The method of claim 1 wherein determining the change comprises correlating the first spatial distribution with the second spatial distribution with different relative offsets and selecting the offset with a greatest correlation.

10. The method of claim 1 further comprising:
displaying an image of the tissue with the imaging system.

11. The method of claim 1 further comprising:
scanning, with the imaging system, the tissue of the patient prior to the heating; and
determining a difference between the scanning prior to the heating and the scanning after the heating;
wherein determining the change in position comprises determining the change as a function of the difference.

12. The method of claim 11 wherein the scanning prior to the heating comprises scanning during a first breathing cycle, and wherein the scanning after the heating comprises scanning during a second breathing cycle, the scanning prior and after each comprising acquiring a sequence of frames of data through the first breathing cycle and the second breathing cycle, respectively.

13. In a non-transitory computer readable storage medium having stored therein data representing instructions executable by a programmed processor for motion tracking in medical treatment, the non-transitory computer readable storage medium comprising instructions for:
applying, with beamformer focused-ultrasound energy from a transducer, a thermal dose in a pattern to tissue within a patient;
imaging, with echoes received at the transducer, detected temperature of the tissue over time; and
determining position of the tissue from the detected temperature of the tissue.

14. The non-transitory computer readable storage medium of claim 13 where applying comprises heating the tissue at locations based on the pattern with ultrasound.

15. The non-transitory computer readable storage medium of claim 13 wherein imaging comprises performing thermometry at different times during a physiological cycle.

16. The non-transitory computer readable storage medium of claim 13 wherein determining the position comprises calculating similarities between frames of data from different times in response to different translations, rotations, scales, or combinations thereof.

17. The non-transitory computer readable storage medium of claim 13 further comprising tracking, as a function of the position, a location of a region in the tissue over time, and guiding treatment of the region as a function of the tracking of the location.

18. A system for motion tracking in medical treatment, the system comprising:
at least one transducer;
a transmit beamformer connected with the at least one transducer, the transmit beamformer operable to transmit, with the at least one transducer, high intensity focused ultrasound into a region;
a receive beamformer connected with the at least one transducer, the receive beamformer operable to receive data representing the region at different times;
a detector configured to determine temperature information in the region; and
a processor configured to track a location in the region subjected to motion from a physiological cycle, the location tracked with the temperature information.

19. The system of claim 18 wherein the transmit beamformer is configured to transmit, with the transducer, the high intensity focused ultrasound in a pattern, and wherein the processor is configured to track based on the pattern, the tracking determining a translation, rotation, or translation and rotation matching the pattern from the data at the different times.

20. The system of claim 18 wherein the detector is configured to determine thermal strain.

* * * * *